(12) United States Patent
Nordström et al.

(10) Patent No.: US 11,339,212 B2
(45) Date of Patent: May 24, 2022

(54) α-SYNUCLEIN PROTOFIBRIL-BINDING ANTIBODIES

(71) Applicant: BioArctic AB, Stockholm (SE)

(72) Inventors: Eva Nordström, Upplands Väsby (SE); Jessica Sigvardson, Spånga (SE); Patrik Nygren, Stockholm (SE)

(73) Assignee: BioArctic AB, Stockholm (SE)

( * ) Notice: Subject to any disclaimer, the term of this patent is extended or adjusted under 35 U.S.C. 154(b) by 0 days.

(21) Appl. No.: 17/359,212

(22) Filed: Jun. 25, 2021

(65) Prior Publication Data
US 2021/0403542 A1 Dec. 30, 2021

Related U.S. Application Data

(60) Provisional application No. 63/071,150, filed on Aug. 27, 2020, provisional application No. 63/044,881, filed on Jun. 26, 2020.

(51) Int. Cl.
C07K 16/18 (2006.01)

(52) U.S. Cl.
CPC .......... *C07K 16/18* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 7,179,463 | B2 | 2/2007 | Lannfelt et al. |
| 7,700,719 | B2 | 4/2010 | Lannfelt et al. |
| 2002/0162129 | A1 | 10/2002 | Lannfelt et al. |
| 2005/0203010 | A1 | 9/2005 | Kim |
| 2006/0018918 | A1 | 1/2006 | Chang |
| 2006/0058233 | A1 | 3/2006 | Schenk et al. |
| 2006/0259986 | A1 | 11/2006 | Chilcote et al. |
| 2007/0248606 | A1 | 10/2007 | Lannfelt et al. |
| 2008/0014194 | A1 | 1/2008 | Schenk et al. |
| 2008/0181902 | A1 | 7/2008 | Lannfelt et al. |
| 2009/0155246 | A1 | 6/2009 | Gellerfors et al. |
| 2009/0258009 | A1 | 10/2009 | Gellerfors et al. |
| 2011/0052498 | A1 | 3/2011 | Lannfelt et al. |
| 2012/0076726 | A1 | 3/2012 | Gellerfors et al. |
| 2012/0100129 | A1 | 4/2012 | Gellerfors et al. |
| 2012/0230912 | A1 | 9/2012 | Gellerfors et al. |
| 2015/0139900 | A1* | 5/2015 | Nordstrom .............. A61P 25/18 424/1.49 |
| 2016/0176970 | A1* | 6/2016 | Corvey ................... A61P 35/02 424/139.1 |
| 2017/0051061 | A1* | 2/2017 | Snyder .................... A61P 35/02 |
| 2019/0135918 | A1* | 5/2019 | Ollier ................. C07K 16/2896 |
| 2019/0330335 | A1* | 10/2019 | Schwabe .................. A61P 1/04 |

FOREIGN PATENT DOCUMENTS

| | | |
|---|---|---|
| WO | WO-00/02053 A2 | 1/2000 |
| WO | WO-02/03911 A2 | 1/2002 |
| WO | WO-2004/041067 A2 | 5/2004 |
| WO | WO-2005/047860 A2 | 5/2005 |
| WO | WO-2006/020581 A2 | 2/2006 |
| WO | WO-2006/045037 A2 | 4/2006 |
| WO | WO-2007/089862 A2 | 8/2007 |
| WO | WO-2009/133521 A2 | 11/2009 |
| WO | WO-2011/104696 A1 | 9/2011 |
| WO | WO-2021/260434 A1 | 12/2021 |

OTHER PUBLICATIONS

Bergstrom et al., Alzheimer's & Dementia: The Journal of the Alzheimer's Association, 2008, vol. 4 (4), T435.
Beyer K. et al., "The Therapeutical Potential of α-Synuclein Antiaggregatory Agents for Dementia with Lewy Bodies," Current Medicinal Chemistry, 2008, vol. 15(26), pp. 2748-2759.
Crews L. et al., "Role of Synucleins in Alzheimer's Disease," Neurotoxicity Research, 2009, vol. 16(3), pp. 306-317.
Davidson W.S et al., "Stabilization of α-Synuclein Secondary Structure Upon Binding to Synthetic Membranes," The Journal of Biological Chemistry, 1998, vol. 273(16), pp. 9443-9449.
Emadi S. et al., "Inhibiting Aggregation of α-Synuclein with Human Single Chain Antibody Fragments," Biochemistry, 2004, vol. 43(10), pp. 2871-2878.
Emadi S. et al., "Isolation of a Human Single Chain Antibody Fragment Against Oligomeric α-Synuclein That Inhibits Aggregation and Prevents α-Synuclein Induced Toxicity," 2007, Journal of Molecular Biology, vol. 368(4), pp. 1132-1144.
International Preliminary Report on Patentability for Application No. PCT/IB2011/050826, dated Aug. 28, 2012.
International Search Report and Written Opinion for Application No. PCT/IB2011/050826, dated Aug. 2, 2011.
International Search Report and Written Opinion for International Application No. PCT/IB2021/000440 dated Nov. 11, 2021.
Kostka M. et al., "Single Particle Characterization of Iron-induced Pore-forming α-Synuclein Oligomers," The Journal of Biological Chemistry, 2008, vol. 283(16), pp. 10992-11003.
Lee M. et al., "Effect of the Overexpression of Wild-type or Mutant α-Synuclein on Cell Susceptibility to Insult," Journal of Neurochemistry, 2001, vol. 76(4), pp. 998-1009.
Lynch S M. et al., "An ScFv Intrabody Against the Non-amyloid Component of α-Synuclein Reduces Intracellular Aggregation and Toxicity," Journal of Molecular Biology, 2008, vol. 377(1), pp. 136-147.
Masliah E. et al., "Effects of α-Synuclein Immunization in a Mouse Model of Parkinson's Disease," Neuron, 2005, vol. 46(6), pp. 857-868.
McGuire-Zeiss et al., Molecular Therapy: The Journal of the American Society of Gene Therapy, 2004, vol. 9 (Supp. 1), S86.
McGuire-Zeiss et al., Biochemical and Biophysical Research Communications, 2006, vol. 349 (4), pp. 1198-1205.

(Continued)

*Primary Examiner* — Adam Weidner
(74) *Attorney, Agent, or Firm* — Foley Hoag LLP

(57) ABSTRACT

The present disclosure is based, in part, on the discovery of antibodies that selectively targets human α-synuclein aggregates such as oligomers/protofibrils, such as BAN0805. BAN0805 has a lower tendency to bind to the undesired monomeric α-synuclein target as compared to mouse monoclonal antibody mAb47.

25 Claims, 4 Drawing Sheets

Specification includes a Sequence Listing.

(56) References Cited

OTHER PUBLICATIONS

Miller T.W. et al., "Intrabody Applications in Neurological Disorders: Progress and Future Prospects," Molecular Therapy: the Journal of the American Society of Gene Therapy, 2005, vol. 12(3), pp. 394-401.

Nannenga B.L. et al., "Anti-oligomeric Single Chain Variable Domain Antibody Differentially Affects Huntingtin and α-Synuclein Aggregates," FEBS Letters, 2008, vol. 582(4), pp. 517-522.

Nasstrom et al., Alzheimer's & Dementia: The Journal of the Alzheimer's Association, 2008, vol. 4 (4), T754.

Nasstrom T. et al., "The Lipid Peroxidation Metabolite 4-oxo-2-nonenal Cross-links α-Synuclein Causing Rapid Formation of Stable Oligomers," Biochemical and Biophysical Research Communications, 2009, vol. 378(4), pp. 872-876.

Papachroni K.K. et al., "Autoantibodies to α-Synuclein in Inherited Parkinson's Disease," Journal of Neurochemistry, 2007, vol. 101(3), pp. 749-756.

Pountney D.L. et al., "Annular α-Synuclein Oligomers Are Potentially Toxic Agents in α-Synucleinopathy. Hypothesis," Neurotoxicity Research, 2005, vol. 7(1-2), pp. 59-67.

Qin et al., "Effect of 4-hydroxy-2-nonenal Modification on α-Synuclein Aggregation," The Journal of Biological Chemistry, 2007, vol. 282 (8), pp. 5862-5870.

Rudikoff S., et al., "Single Amino Acid Substitution Altering Antigen-binding Specificity," Proceedings of the National Academy of Sciences of the United States of America, 1982, vol. 79(6), pp. 1979-1983.

Shtilerman M.D. et al., "Molecular Crowding Accelerates Fibrillization of α-Synuclein: Could an Increase in the Cytoplasmic Protein Concentration Induce Parkinson's Disease?" Biochemistry, 2002, vol. 41(12), pp. 3855-3860.

Trostchansky A. et al., "Interaction with Phospholipids Modulates α-Synuclein Nitration and Lipid-protein Adduct Formation," The Biochemical Journal, 2006, vol. 393(Pt 1), pp. 343-349.

Wahlberg et al., Alzheimer's & Dementia: The Journal of the Alzheimer's Association, 2008, vol. 4 (4), T481-482.

Zhou, et al., Molecular Therapy, Academic Press, 2004, vol. 10(6), pp. 1023-1031.

\* cited by examiner

FIG. 1

| Temperature Stress: 47HKKA | Major peak (monomer) | | | |
|---|---|---|---|---|
| Temperature (degree C) | 4 | 25 | 37 | 50 |
| Mw (kDa) | 134.45 | 134.22 | 134.43 | 134.66 |
| (±) | 0.47 | 0.32 | 0.44 | 0.30 |
| Polydispersity (Mw / Mn) | 1.00 | 1.00 | 1.00 | 1.00 |
| (±) | 0.00 | 0.00 | 0.00 | 0.00 |
| acceptable < 1.05 | | | | |
| Mass fraction (%) acceptable > 95 % | 100 | 100 | 100 | 99.4 |
| | Sample (if > 1 peak) | | | |
| Polydispersity (Mw / Mn) | n/a | n/a | n/a | 1.01 |
| (±) | | | | 0.00 |
| Mass fraction (%) | n/a | n/a | n/a | 100 |
| Comment | The SEC-MALS analysis shows some aggregation at 50 degrees C, but the amount is negligible (< 5%). All samples pass the temperature stability assay. | | | |

α-SYNUCLEIN PROTOFIBRIL-BINDING ANTIBODIES

CROSS-REFERENCE TO RELATED APPLICATIONS

This application claims the benefit of U.S. Provisional Application No. 63/044,881, filed Jun. 26, 2020, and U.S. Provisional Application No. 63/071,150, filed Aug. 27, 2020, the content of each of which is incorporated by reference herein in its entirety.

REFERENCE TO SEQUENCE LISTING

Incorporated herein by reference in its entirety is a Sequence Listing entitled Sequence_Listing_AVR-71901_ST25.txt, comprising SEQ ID NO: 1 through SEQ ID NO: 20, which includes the nucleic acid and amino acid sequences disclosed herein. The Sequence Listing has been submitted electronically herewith in ASCII text format via EFS. The Sequence Listing was first created on Jun. 25, 2021 and is 18,417 bytes in size.

BACKGROUND

International Patent Application No. WO2011/104696 A1 (which is incorporated herein by reference) discloses a murine monoclonal IgG antibody mAb47, which binds to protofibril forms of α-synuclein. There remains a need for antibodies that selectively bind to protofibril forms of α-synuclein that are suitable for use in humans.

SUMMARY

The present disclosure relates to antibodies having high affinity for human α-synuclein protofibrils and low affinity for α-synuclein monomers. In some embodiments, the antibodies described herein selectively target human α-synuclein aggregates such as oligomers/protofibrils, i.e., with a much stronger binding to α-synuclein protofibrils compared to monomer. In some embodiments, the antibodies described herein have better selectivity than mAb47 when comparing the α-synuclein protofibril versus monomer binding ratios. In some embodiments, the antibodies described herein are anti-α-synuclein antibodies.

In one aspect, the present disclosure relates to BAN0805, a monoclonal antibody comprising a heavy chain comprising an amino acid sequence set forth in SEQ ID NO:3 and a light chain comprising an amino acid sequence set forth in SEQ ID NO:4 that selectively targets human α-synuclein aggregates such as oligomers/protofibrils with high affinity for human α-synuclein protofibrils and low affinity for α-synuclein monomers. Interestingly, BAN0805 also exhibits lower α-synuclein monomer binding than mAb47, resulting in better selectivity for BAN0805 than for mAb47 when comparing the α-synuclein protofibril versus monomer binding ratios. Additionally, binding to β- and γ-synuclein monomer or Aβ-protofibrils was not detected for BAN0805.

The present disclosure further relates to antibodies for improvements in treating neurodegenerative disorders with α-synuclein pathology, including, but not limited to, Parkinson's disease (PD).

BRIEF DESCRIPTION OF THE DRAWINGS

FIG. 1 shows heat stress data for BAN0805. Samples of the purified candidate antibodies at 1 mg/mL were exposed to temperatures of a) 4° C., b) 25° C., c) 37° C. and d) 50° C. for two weeks. Samples were then analyzed by SEC-MALS to check for aggregation. The data suggest there are no aggregation concerns for BAN0805 due to heat stress.

DETAILED DESCRIPTION

Figure 2:
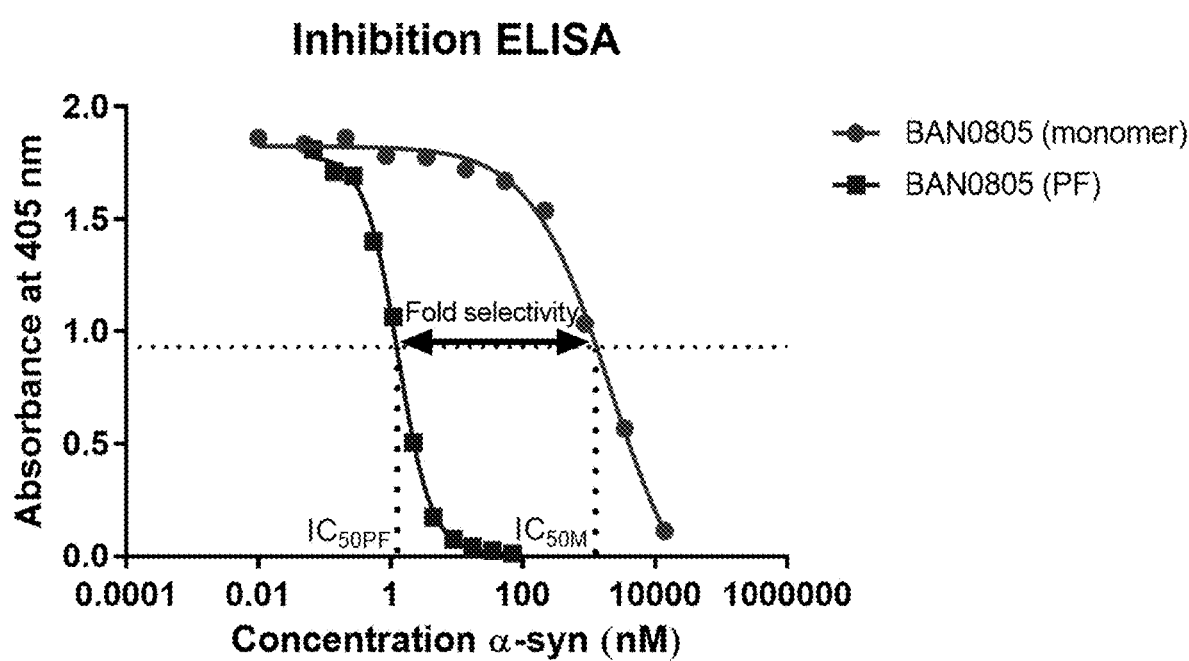
FIG. 2 shows the inhibition ELISA with $IC_{50}$ values for BAN0805 when bound to α-synuclein monomers and protofibrils (PF). BAN0805 has a 910-fold better selectivity for the protofibril form of α-synuclein compared to mAb47 which only has a 340-fold selectivity (not shown). The protofibril level was expressed as equivalent to monomer level in concentration and the size of the protofibrils was not considered. The fold selectivity was calculated by dividing the $IC_{50}$ value for the monomer binding with the $IC_{50}$ value for the PF binding.

The present disclosure relates to antibodies having high affinity for human α-synuclein protofibrils and low affinity for α-synuclein monomers.

As disclosed herein, the present disclosure relates to the following embodiments.

Embodiment 1. An antibody comprising a heavy chain comprising the amino acid sequence of SEQ ID NO: 1 and a light chain comprising the amino acid sequence of SEQ ID NO: 2.

Embodiment 2. The antibody of embodiment 1, wherein the antibody is of the IgG isotype.

Embodiment 3. The antibody of embodiment 1, wherein the antibody is of the IgG4 isotype.

Embodiment 4. The antibody of any one of embodiments 1-3, wherein the antibody has a $K_D$ value for binding the protofibril form of α-synuclein at least 110,000 times smaller than the $K_D$ value for binding the monomeric form of α-synuclein.

Embodiment 5. The antibody of any one of embodiments 1-3, wherein the antibody has a $K_D$ value for binding the protofibril form of α-synuclein of at most 18 pM and a $K_D$ value for binding the monomeric form of α-synuclein of at least 2200 nM.

Embodiment 6. The antibody of either embodiment 4 or 5, wherein the $K_D$ of said antibody for binding to the protofibril form of α-synuclein and the $K_D$ of said antibody for binding to the monomeric form of α-synuclein are measured by SPR.

Embodiment 7. An antibody comprising a heavy chain comprising the amino acid sequence of SEQ ID NO: 3 and a light chain comprising the amino acid sequence of SEQ ID NO: 4.

Embodiment 8. The antibody of embodiment 7, wherein the antibody comprises two heavy chains and two light chains.

Embodiment 9. A nucleic acid encoding a polypeptide comprising an amino acid sequence selected from the group consisting of SEQ ID NOs: 1-4.

Embodiment 10. The nucleic acid of embodiment 9, comprising a sequence selected from the group consisting of SEQ ID NOs: 11-14 and 17-20.

Embodiment 11. One or more nucleic acids encoding the antibody of any one of embodiments 1 to 8.

Embodiment 12. The one or more nucleic acids of embodiment 11, wherein
(a) the one or more nucleic acids comprise the sequences of SEQ ID NOs: 11 and 12,
(b) the one or more nucleic acids comprise the sequences of SEQ ID NOs: 13 and 14,
(c) the one or more nucleic acids comprise the sequences of SEQ ID NOs: 17 and 18, or
(d) the one or more nucleic acids comprise the sequences of SEQ ID NOs: 19 and 20.

Embodiment 13. One or more vector(s) comprising the nucleic acid(s) of any one of embodiments 9, 10, 11 or 12.

Embodiment 14. A host cell comprising the nucleic acid(s) of any one of embodiments 9 to 12.

Embodiment 15. A host cell comprising the one or more vector(s) of embodiment 13.

Embodiment 16. A host cell expressing the antibody of any one of embodiments 1-8.

Embodiment 17. A composition comprising at least one antibody of any one of embodiments 1-8, and a pharmaceutically acceptable carrier.

In one aspect, the present disclosure relates to an antibody having a high affinity for human α-synuclein protofibrils and low affinity of α-synuclein monomers, and comprising a heavy chain comprising the amino acid sequence of SEQ ID NO: 1, and a light chain comprising the amino acid sequence of SEQ ID NO: 2.

In one embodiment, the antibodies provided herein comprise a heavy chain comprising the amino acid sequence of SEQ ID NO: 1 and a light chain comprising the amino acid sequence of SEQ ID NO: 2.

In one embodiment, the antibodies provided herein comprise a heavy chain comprising the amino acid sequence of SEQ ID NO:3 and a light chain comprising the amino acid sequence of SEQ ID NO:4. In some embodiments, the antibodies provided herein comprise two heavy chains and two light chains.

In one embodiment, the antibody described in the present disclosure is of the IgG isotype, in particular human IgG isotype. In another embodiment, the antibody is of the IgG4 isotype.

Within the present disclosure, high affinity to human α-synuclein protofibrils refers to a dissociation constant $K_D$ of less than $10^{-7}$ M for human α-synuclein protofibrils. Accordingly, in one embodiment, the antibodies described in the present disclosure have a $K_D$ of less than $10^{-8}$, $10^{-9}$, $10^{-10}$, $10^{-11}$ M, or $10^{-12}$ M for human α-synuclein protofibrils. In specific embodiments, the antibodies comprise a heavy chain comprising an amino acid sequence set forth in SEQ ID NO: 1 and a light chain comprising an amino acid sequence set forth in SEQ ID NO: 2, and have a $K_D$ of 11.2 to 25.8 pM for human α-synuclein protofibrils.

In another embodiment, the antibodies comprise a heavy chain comprising the amino acid sequence of SEQ ID NO: 1 and a light chain comprising the amino acid sequence of SEQ ID NO: 2, and have low affinity to human α-synuclein monomer. For example, the $K_D$ of the antibodies described in the present disclosure for binding to the monomeric form of α-synuclein is at least 1500 nM, at least 1600 nM, at least 1700 nM, at least 1800 nM, at least 1900 nM, at least 2000 nM, at least 2100 nM, at least 2200 nM, at least 2300 nM, at least 2400 nM, at least 2500 nM, at least 2600 nM, at least 2700 nM, at least 2800 nM, at least 2900 nM, or at least 3000 nM. In specific embodiments, the antibodies comprise a heavy chain comprising an amino acid sequence set forth in SEQ ID NO: 1 and a light chain comprising an amino acid sequence set forth in SEQ ID NO: 2, and have a $K_D$ of 1650 nM to 2730 nM for the human α-synuclein monomer.

In one embodiment, the antibodies comprise a heavy chain comprising the amino acid sequence of SEQ ID NO: 1 and a light chain comprising the amino acid sequence of SEQ ID NO: 2, and have greater than 80,000 fold, greater than 90,000 fold, greater than 100,000 fold, greater than 110,000 fold, or greater than 120,000 fold selectivity to human α-synuclein protofibril versus monomeric α-synuclein. In specific embodiments, the antibodies comprise a heavy chain comprising an amino acid sequence set forth in SEQ ID NO: 1 and a light chain comprising an amino acid sequence set forth in SEQ ID NO: 2, and have a 64,000 fold to 244,000 fold selectivity to human α-synuclein protofibril versus monomeric α-synuclein.

In one embodiment, these binding affinities are measured using inhibition ELISA, for example, as described in example 3. In another embodiment, these binding affinities are measured by Surface Plasmon Resonance (SPR), for example, as described in example 3.

In another aspect, provided herein are nucleic acids encoding at least one polypeptide comprising an amino acid sequence selected from the group consisting of SEQ ID NOs: 1-4. The nucleic acid can be DNA or RNA. The nucleic acid may comprise a sequence selected from the group consisting of SEQ ID NOs: 11-14 and 17-20.

In another aspect, provided herein are one or more nucleic acids encoding an antibody of the invention. In one embodiment, the one or more nucleic acids comprise the sequences of SEQ ID Nos: 11 and 12. In another embodiment, the one or more nucleic acids comprise the sequences of SEQ ID Nos: 13 and 14. In one embodiment, the one or more nucleic acids comprise the sequences of SEQ ID Nos: 17 and 18. In one embodiment, the one or more nucleic acids comprise the sequences of SEQ ID Nos: 19 and 20.

In another aspect, provided herein are vectors comprising nucleic acids that encode at least one polypeptide comprising an amino acid sequence selected from the group consisting of SEQ ID NOs: 1-4. Such vectors include but are not limited to cloning vectors or expression vectors. In one aspect, one or more vectors are providing encoding an antibody of the invention. In one embodiment, the one or more vectors comprise the sequences of SEQ ID Nos: 11 and 12. In another embodiment, the one or more vectors comprise the sequences of SEQ ID Nos: 13 and 14. In one embodiment, the one or more vectors comprise the sequences of SEQ ID Nos: 17 and 18. In one embodiment, the one or more vectors comprise the sequences of SEQ ID Nos: 19 and 20.

In another aspect, provided herein are host cells comprising nucleic acids that encode at least one polypeptide comprising an amino acid sequence selected from the group consisting of SEQ ID NOs: 1-4. In one embodiment, the host cells comprise nucleic acid(s) encoding an antibody of the invention. The host cells described herein may be mammalian cells, such as B cells, hybridomas, or CHO cells. In one embodiment, the host cells described herein are human cells.

In another aspect, provided herein is a composition comprising an antibody of the invention and a pharmaceutically acceptable excipient.

EXAMPLES

Example 1—Generation of Antibody Candidates

The initial variants of mAb47 were generated by direct grafting of mAb47 CDRs to human framework sequences, and making back-mutations to the mouse residues at various positions. None of the initial variants showed desired binding properties to α-synuclein. Therefore, a new model was built and analyzed to find more possible mutations for generating new variants.

In the second attempt to improve mAb47, less likely residues that interact with the target and the residues at 4 Å from the CDRs determined were checked. An antibody variant having a heavy chain sequence set forth in SEQ ID NO: 3 and a light chain sequence set forth in SEQ ID NO: 4 was generated and named as BAN0805. It was found that the back mutations V71K and R94K, while simultaneously present in BAN0805, are crucial for the binding capacity of these antibodies as their removal in the other variants have resulted in a loss of binding.

Since BAN0805 has one less back mutation than a comparable variant, and has shown binding and selectivity for protofibrils over monomer species, BAN0805 was chosen as the lead candidate.

Example 2—Characterization of Antibody Candidates

To determine thermal stability, the antibodies were subjected to higher temperatures for 10 minutes, cooled to 4° C. and used in an ELISA assay at the $EC_{80}$ concentration of each candidate (usually 5-50 ng/mL). BAN0805 was stable, retaining its binding ability to α-synuclein up to 75° C. where it started to decrease, while the chimeric mouse antibody c47 or cmAb47 (the chimera combining human IgG4 and the variable region of mAb47) binding dropped drastically around 5° C. earlier.

In order to determine the melting temperature of the antibodies, cmAb47 was tested against BAN0805 in a thermal shift assay. Melting temperature data indicates that the Tm for BAN0805 was calculated to be 65-65.4° C., lower than the chimeric at 70° C.

Additionally, purified samples at 1 mg/mL were injected at 0.4 mL/min into a size exclusion column in an HPLC system and analyzed by multi-angle light scattering to determine the absolute molar masses and check for aggregation. The data suggest there were no aggregation concerns for BAN0805. BAN0805 was monodispersed (Mw/Mn<1.05). The mass recovery was 100% (calculated mass over injected mass), which indicates good protein recovery.

Cross-Interaction Chromatography using bulk purified human polyclonal IgG is a technique for monitoring non-specific protein-protein interactions, and can be used to discriminate between soluble and insoluble antibodies. An elevated Retention Index (k') indicates a self-interaction propensity and a low solubility. BAN0805 showed a Retention Index of 0.025 which is below 0.035 of the cmAb47, indicating a low propensity for non-specific interactions and good solubility.

For freeze/thaw stress analysis, samples of the purified candidate antibodies at 1 mg/mL were subjected to 10 cycles of 15 minutes at −80° C. followed by thawing for 15 minutes at Room Temperature. For heat-induced stress analysis, samples of the purified candidate antibodies at 1 mg/mL were exposed to temperatures of a) 4° C., b) 25° C., c) 37° C. and d) 50° C. for two weeks. Samples were then analyzed by SEC-MALS to check for aggregation. The data suggest that freeze thaw cycles and heat stress did not cause aggregation in BAN0805. See FIG. 1.

BAN0805 was analyzed and compared to the closest germline (IGVH4-59*03/IGHJ3*01 for HK and IGVK2-28*01/IGKJ2*02 for KA) following IMGT CDR definitions and the DomainGapAlign tool. Overall identity to human germline was 86.5% for the light chain, above the 85% cutoff for it to be considered humanized for this analysis. For the heavy chain, after grafting CDRs and introducing two mouse back mutations, the percentage identity to human germline dropped to just under 81%. This might be explained by the fact that the IMGT CDR2 is significantly shorter than the Kabat definition used here, which caused the insertion of a higher number of mouse residues at the beginning of the framework 3.

Example 3—Selective Binding of BAN0805 to Human α-Synuclein Protofibrils

Binding selectivity of BAN0805 to human α-synuclein protofibrils were measured by both inhibition ELISA and Surface Plasmon Resonance (SPR).

The $IC_{50}$ values for α-synuclein protofibril were very similar for mAb47 and BAN0805 (2.7 nM and 2.2 nM respectively) showing that the binding characteristics to protofibril did not change after humanization. In contrast, binding to α-synuclein monomer did change, resulting in a reduced binding strength of BAN0805 to α-synuclein monomer. This resulted in better selectivity for α-synuclein protofibril versus monomer for BAN0805 (910-fold) compared to mAb47 (340-fold). See FIG. 2.

However, due to detection limitations it was not possible to lower the antibody concentration further to make it possible to detect even lower $IC_{50}$ values and hence approach the "true" $IC_{50}$ value. Therefore, the $IC_{50}$ values presented have been obtained according to the current procedure for the inhibition ELISA which has been used for all mAb47 and BAN0805 batches, with the notion that $IC_{50}$ values for the protofibril are likely overestimated (i.e., the binding strength is likely underestimated). A more accurate binding and hence selectivity were obtained using SPR which is described below.

Figure 3:
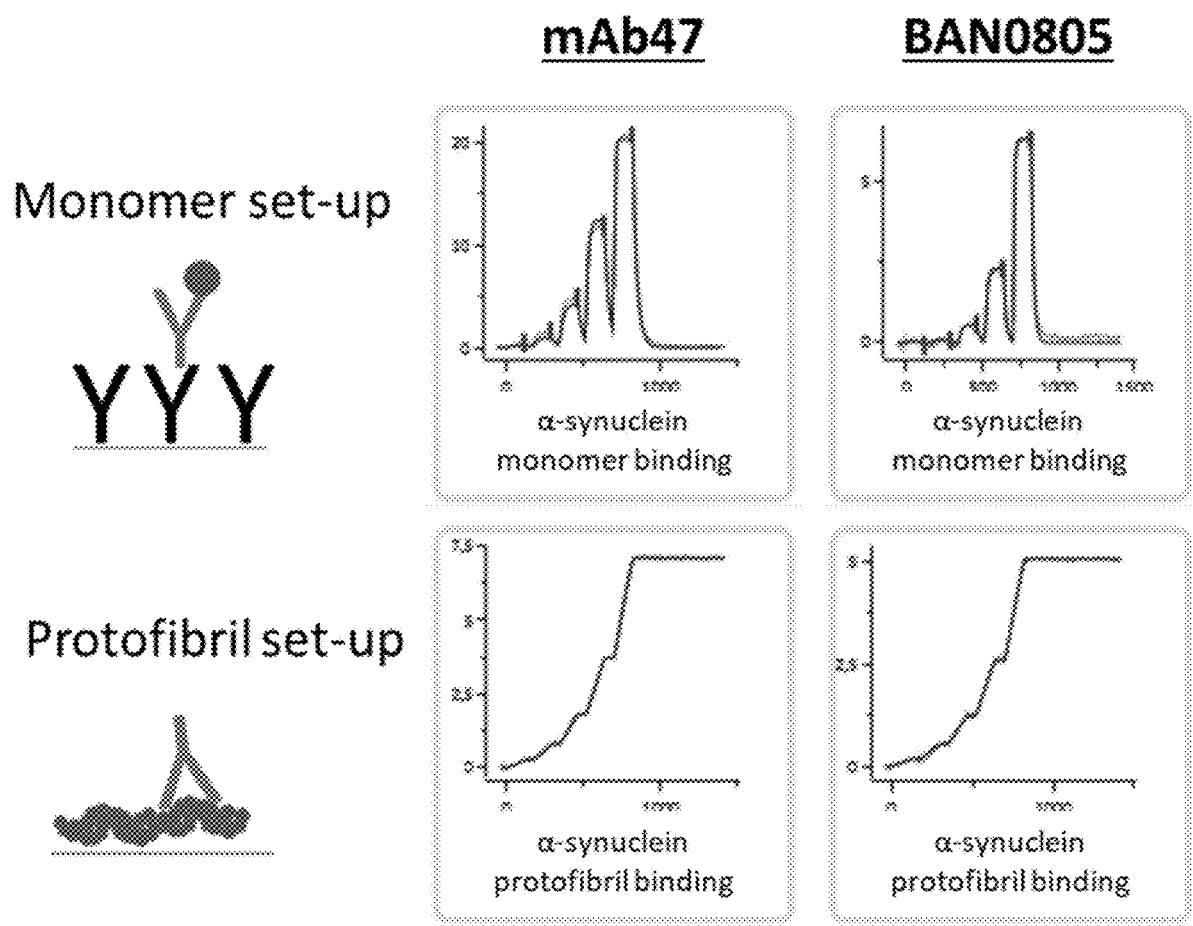
FIG. 3 shows binding and selectivity for BAN0805 compared to mAb47 using Biacore SPR. The $K_D$ values for α-synuclein protofibril were similar for mAb47 and BAN0805, showing that the modification of mAb47 did not affect the strong binding to α-synuclein protofibril, confirming the results from the inhibition ELISA. The $K_D$ values measured with SPR resulted in a 110,000-fold and 18,000-fold selectivity for PF vs monomer for BAN0805 and mAb47, respectively. Representative sensorgrams of mAb47 and BAN0805 SPR measurements on Biacore 8K are shown.

The binding selectivity of mAb47 and BAN0805 was confirmed by SPR using a Biacore 8K instrument (GE Healthcare). Due to feasibility issues caused by the complexity of the target antigen in combination with pronounced avidity dependence of the antibodies, different assay set-ups were used to assess α-synuclein protofibril and monomer binding, respectively. For measurements of binding to monomer, the chip was coated with an anti-mouse or anti-human antibody for mAb47 and BAN0805, respectively. 0.25-1.5 µg/ml mAb47 or BAN0805 was then captured on the surface, followed by a 5-fold dilution single cycle kinetics injection of α-synuclein monomer. To measure binding to protofibril (PF), the chip was coated with 0.5 µg/ml PF and a 2-fold dilution of mAb47 or BAN0805 was injected using single cycle kinetics. Representative sensorgrams for mAb47 and BAN0805 are shown in FIG. 3.

The $K_D$ values for α-synuclein protofibril were similar for mAb47 and BAN0805, showing that the modification of mAb47 did not affect the strong binding to α-synuclein protofibril (Table 1), confirming the results from the inhibition ELISA. However, the $K_D$ values were in the pM range, confirming the afore-mentioned limitations with the inhibition ELISA. Importantly, it was confirmed by the SPR that the affinity of BAN0805 for α-synuclein monomer was reduced in comparison to mAb47. The $K_D$ values measured with SPR resulted in a 110,000-fold and 18,000-fold selectivity for PF versus monomer for BAN0805 and mAb47, respectively. Average $K_D$ values for mAb47 and BAN0805 for α-synuclein monomer and protofibril are shown in Table 1.

TABLE 1

KD values for mAb47 and BAN0805 for binding to α-synuclein protofibril (PF) and monomer (M) by Biacore SPR.

| Antibody | α-synuclein PF $K_D$ (pM) | α-synuclein monomer $K_D$ (nM) | Selectivity PF vs. monomeric α-synuclein (fold) |
|---|---|---|---|
| BAN0805 | 18.5 ± 7.3 (n = 27) | 2190 ± 540 (n = 59) | 110 000 |
| mAb47 | 16.8 ± 8.0 (n = 18) | 307 ± 35 (n = 23) | 18 000 |

Figure 4:
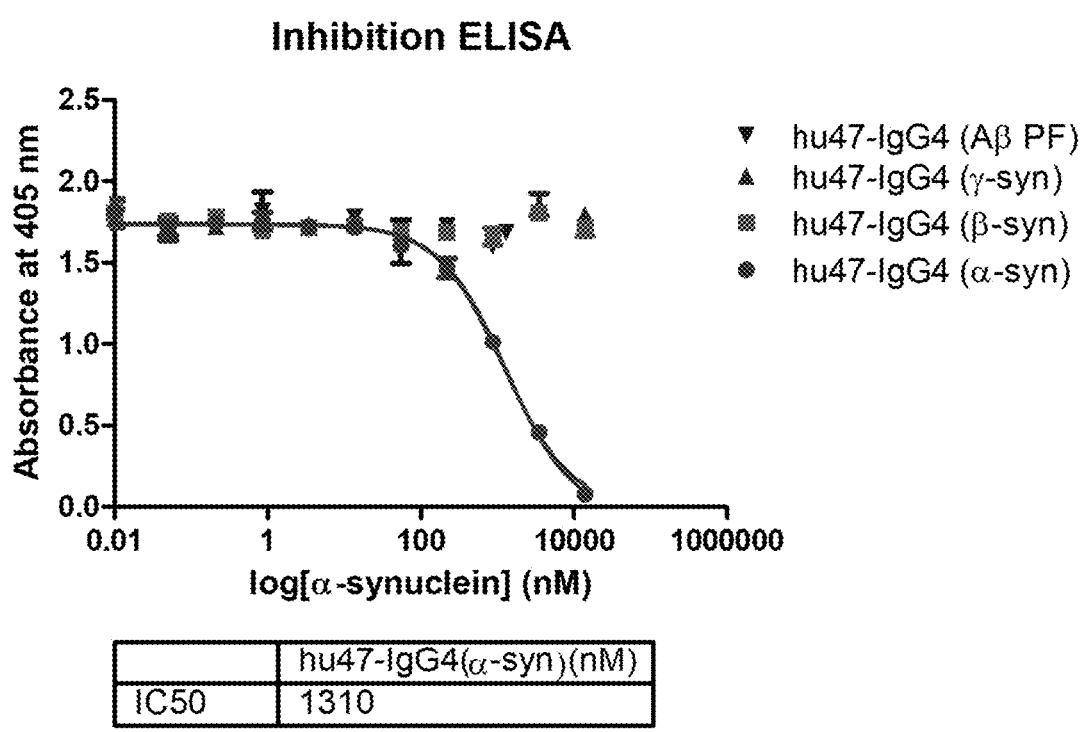
FIG. 4 shows cross-reactivity of BAN0805, here referred to as hu47-IgG4 to α-synuclein monomer, β-synuclein monomer, γ-synuclein monomer and Aβ-protofibril using inhibition ELISA. The result showed no detectable binding to β- or γ-synuclein monomer or Aβ-protofibril.

Data are presented as Mean ± Standard deviation (n = Number of experiments)
$K_D$: Dissociation constant The cross-reactivity of homologous proteins, such as β- or γ-synuclein, and other aggregation prone proteins like Aβ was tested using both direct ELISA (where dense coating mimics aggregated forms of the coated protein), as well as inhibition ELISA. Here, the cross-reactivity of mAb47 and BAN0805, was analyzed side-by-side by inhibition ELISA. The inhibition ELISA was performed with β-synuclein monomer, γ-synuclein monomer and Aβ-protofibril as antigens. The result indicates there was no detectable binding of BAN0805 to β- or γ-synuclein monomer or Aβ-protofibril. A representative BAN0805 cross-reactivity test to β- or γ-synuclein in inhibition ELISA is shown in FIG. 4. Data are presented in Table 2.

TABLE 2

Cross-reactivity of mAb47 and BAN0805 to β-synuclein monomer, γ-synuclein monomer and Aβ-protofibril.

| Antibody | β-synuclein monomer (>14 μM) | γ-synuclein monomer (>14 μM) | Aβ-protofibril (>5 μM) |
|---|---|---|---|
| BAN0805 | n.b. | n.b. | n.b. |
| mAb47 | n.b. | n.b. | n.b. | n.b. = no binding

Results from inhibition ELISA and the Surface Plasmon Resonance (SPR) Biacore data both showed the affinity of BAN0805 for α-synuclein monomer was reduced in comparison to mAb47, indicating a better selectivity of BAN0805 compared to mAb47. Additionally, no binding to β- and γ-synuclein monomer or Aβ-protofibrils was seen at concentrations tested (up to μM range) for BAN0805.

Thus, the present disclosure relates to an antibody having high affinity for α-synuclein protofibrils and low affinity to α-synuclein monomers, and having the following characteristics compared to murine mAb47:

(1) BAN0805 has a much stronger binding to α-synuclein protofibrils compared to monomer;

(2) both inhibition ELISA and SPR Biacore data showed that the α-synuclein monomer binding was stronger for mAb47 compared to BAN0805 resulting in better selectivity for BAN0805 than for mAb47 when comparing the α-synuclein protofibril versus monomer binding ratios (i.e., BAN0805 has a lower tendency to bind to the undesired monomeric α-synuclein target as compared to mAb47); and (3) no binding to β- and γ-synuclein monomer or Aβ-protofibrils was seen at concentrations tested (up to μM range) for BAN0805.

Example 4—Production of BAN0805

To produce BAN0805, optimized DNA sequences encoding BAN0805 VH (SEQ ID NO: 13) and VL (SEQ ID NO: 14) including signal peptides were synthesized and cloned into GS vectors pXC-IgG4Pro(deltaK) and pXC-Kappa (Lonza), respectively. The resulting HC and LC SGVs were then used to generate a double gene vector (DGV) containing both the HC and LC genes. The optimized DNA sequences encoding BAN0805 heavy chain (HC) and light chain (LC) are set forth in SEQ ID NOs: 11 and 12, respectively. The optimized DNA sequences encoding BAN0805 heavy chain variable region (VH) and light chain variable region (VL) are set forth in SEQ ID NOs: 13 and 14, respectively. SEQ ID NOs: 11-14 all include a nucleotide sequence encoding a signal peptide (see Table 3B). The nucleotide sequences corresponding to amino acid sequences for BAN0805 HC, LC, VH, and VL excluding the signal peptide are set forth in SEQ ID NOs: 17, 18, 19 and 20, respectively. The CDR sequences of BAN0805 are listed in Table 3A. The amino acid sequences of heavy chain CDR (VH-CDR) 1-3 according to Chothia nomenclature are set forth in SEQ ID NOs: 5, 6, and 7, respectively. The amino acid sequences of heavy chain CDR (VH-CDR) 1-3 according to Kabat nomenclature are set forth in SEQ ID NOs: 15, 16, and 7, respectively. The amino acid sequence of heavy chain CDR (VH-CDR-3) according to Chothia and Kabat nomenclatures is the same and set forth in SEQ ID NO: 7. The amino acid sequences of light chain CDR (VL-CDR) 1-3 according to Chothia and Kabat nomenclatures are the same, and set forth in SEQ ID NOs: 8, 9, and 10, respectively.

The resultant DGV, termed pBAN0805/DGV, was then transiently transfected to CHOK1SV GS-KO cells, and cultured under conditions which resulted in the secretion of assembled antibody. The secreted antibody was then purified by Protein A affinity chromatography.

TABLE 3

SEQUENCE LISTING

A. BAN0805
VH:
(SEQ ID NO: 1)
QVQLQESGPGLVKPSETLSLTCTVSGFSLTSYGVHWIRQPPGKGLEWIGV

IWRGGSTDYSAAFMSRLTISKDTSKNQVSLKLSSVTAADTAVYYCAKLLR

SVGGFADWGQGTMVTVSS

VL:
(SEQ ID NO: 2)
DIVMTQSPLSLPVTPGEPASISCRSSQTIVHNNGNTYLEWYLQKPGQSPQ

LLIYKVSNRFSGVPDRFSGSGSGTDFTLKISRVEAEDVGVYYCFQGSHVP

FTFGQGTKLEIK

Heavy Chain
(SEQ ID NO: 3)
QVQLQESGPGLVKPSETLSLTCTVSGFSLTSYGVHWIRQPPGKGLEWIGV

IWRGGSTDYSAAFMSRLTISKDTSKNQVSLKLSSVTAADTAVYYCAKLLR

TABLE 3-continued

SEQUENCE LISTING

SVGGFADWGQGTMVTVSSASTKGPSVFPLAPCSRSTSESTAALGCLVKDY
FPEPVTVSWNSGALTSGVHTFPAVLQSSGLYSLSSVVTVPSSSLGTKTYT
CNVDHKPSNTKVDKRVESKYGPPCPPCPAPEFLGGPSVFLFPPKPKDTLM
ISRTPEVTCVVVDVSQEDPEVQFNWYVDGVEVHNAKTKPREEQFNSTYRV
VSVLTVLHQDWLNGKEYKCKVSNKGLPSSIEKTISKAKGQPREPQVYTLP
PSQEEMTKNQVSLTCLVKGFYPSDIAVEWESNGQPENNYKTTPPVLDSDG
SFFLYSRLTVDKSRWQEGNVFSCSVMHEALHNHYTQKSLSLSLG

Light Chain
(SEQ ID NO: 4)
DIVMTQSPLSLPVTPGEPASISCRSSQTIVHNNGNTYLEWYLQKPGQSP
QLLIYKVSNRFSGVPDRFSGSGSGTDFTLKISRVEAEDVGVYYCFQGSHV
PFTFGQGTKLEIKRTVAAPSVFIFPPSDEQLKSGTASVVCLLNNFYPREA
KVQWKVDNALQSGNSQESVTEQDSKDSTYSLSSTLTLSKADYEKHKVYAC
EVTHQGLSSPVTKSFNRGEC CDRs
VH-CDR-1 (Chothia):
(SEQ ID NO: 5)
GFSLTSYGVH VH-CDR-1 (Kabat):
(SEQ ID NO: 15)
SYGVH VH-CDR-2 (Chothia):
(SEQ ID NO: 6)
VIWRGGSTDYSAAF VH-CDR-2 (Kabat):
(SEQ ID NO: 16)
VIWRGGSTDYSAAFMS VH-CDR-3 (Kabat/Chothia):
(SEQ ID NO: 7)
LLRSVGGFAD VL-CDR-1 (Kabat/Chothia):
(SEQ ID NO: 8)
RSSQTIVHNNGNTYLE VL-CDR-2 (Kabat/Chothia):
(SEQ ID NO: 9)
KVSNRFS VL-CDR-3 (Kabat/Chothia):
(SEQ ID NO: 10)
FQGSHVPFT Table 3A lists underlined sequences as CDR sequences according to Chothia nomenclature and bold sequences as CDR sequences according to Kabat nomenclature. CDR1, CDR2, and CDR3 are shown in standard order of appearance from left (N-terminus) to right (C-terminus).

B. Nucleotide Sequences Encoding BAN0805 Heavy and Light Chains BAN0805 HC gene with signal sequence
(SEQ ID NO: 11)
<u>ATGGAATGGTCCTGGGTGTTCCTGTTCTTCCTGTCCGTGACCACCGGCGT</u>
<u>GCACTCT</u>CAGGTTCAGCTGCAAGAGTCTGGCCCTGGCCTGGTCAAGCCTT
CCGAAACACTGTCTCTGACCTGCACCGTGTCCGGCTTCTCCCTGACATCT
TATGGGGTGCACTGGATCAGACAGCCTCCAGGCAAAGGCCTGGAATGGAT
CGGAGTGATTTGGAGAGGCGGCTCCACCGATTACTCCGCCGCCTTCATGT
CCCGGCTGACCATCTCTAAGGACACCTCCAAGAACCAGGTGTCCCTGAAG
CTGTCCTCTGTGACCGCTGCTGATACCGCCGTGTACTACTGTGCCAAGCT
GCTGAGATCTGTCGGCGGCTTTGCTGATTGGGGCCAGGGCACAATGGTCA
CCGTGTCTAGCGCTTCTACAAAGGGCCCAAGCGTGTTCCCCCTGGCCCCC
TGCTCCAGAAGCACCAGCGAGAGCACAGCCGCCCTGGGCTGCCTGGTGAA
GGACTACTTCCCCGAGCCCGTGACCGTGTCCTGGAACAGCGGAGCCCTGA
CCAGCGGCGTGCACACCTTCCCCGCCGTGCTGCAGAGCAGCGGCCTGTAC
AGCCTGAGCAGCGTGGTGACCGTGCCCAGCAGCAGCCTGGGCACCAAGAC
CTACACCTGTAACGTGGACCACAAGCCCAGCAACACCAAGGTGGACAAGA
GGGTGGAGAGCAAGTACGGCCCACCCTGCCCCCCCTGCCCAGCCCCCGAG
TTCCTGGGCGGACCCAGCGTGTTCCTGTTCCCCCCCAAGCCCAAGGACAC
CCTGATGATCAGCAGAACCCCCGAGGTGACCTGTGTGGTGGTGGACGTGT
CCCAGGAGGACCCCGAGGTCCAGTTCAACTGGTACGTGGACGGCGTGGAG
GTGCACAACGCCAAGACCAAGCCCAGAGAGGAGCAGTTTAACAGCACCTA
CCGGGTGGTGTCCGTGCTGACCGTGCTGCACCAGGACTGGCTGAACGGCA
AAGAGTACAAGTGTAAGGTCTCCAACAAGGGCCTGCCAAGCAGCATCGAA
AAGACCATCAGCAAGGCCAAGGGCCAGCCTAGAGAGCCCCAGGTCTACAC
CCTGCCACCCAGCCAAGAGGAGATGACCAAGAACCAGGTGTCCCTGACCT
GTCTGGTGAAGGGCTTCTACCCAAGCGACATCGCCGTGGAGTGGGAGAGC
AACGGCCAGCCCGAGAACAACTACAAGACCACCCCCCCAGTGCTGGACAG
CGACGGCAGCTTCTTCCTGTACAGCAGGCTGACCGTGGACAAGTCCAGAT
GGCAGGAGGGCAACGTCTTTAGCTGCTCCGTGATGCACGAGGCCCTGCAC
AACCACTACACCCAGAAGAGCCTGAGCCTGTCCCTGGGCTGATGA BAN0805 LC gene with signal sequence
(SEQ ID NO: 12)
<u>ATGTCTGTGCCTACACAGGTTCTGGGACTGCTGCTGCTGTGGCTGACCGA</u>
<u>CGCCAGATGC</u>GACATCGTGATGACCCAGTCTCCACTGAGCCTGCCTGTGA
CACCTGGCGAGCCTGCTTCCATCTCCTGCAGATCCTCTCAGACCATCGTG
CACAACAACGGCAACACCTACCTGGAATGGTATCTGCAGAAGCCCGGCCA
GTCTCCTCAGCTGCTGATCTACAAGGTGTCCAACCGGTTCTCTGGCGTGC
CCGACAGATTTTCCGGCTCTGGCTCTGGCACCGACTTCACCCTGAAGATC
TCCAGAGTGGAAGCCGAGGACGTGGGCGTGTACTACTGCTTCCAAGGCTC
TCACGTGCCCTTCACCTTTGGCCAGGGCACCAAGCTGGAAATCAAGCGTA
CGGTGGCCGCTCCCAGCGTGTTCATCTTCCCCCCAAGCGACGAGCAGCTG
AAGAGCGGCACCGCCAGCGTGGTGTGTCTGCTGAACAACTTCTACCCCAG
GGAGGCCAAGGTGCAGTGGAAGGTGGACAACGCCCTGCAGAGCGGCAACA
GCCAGGAGAGCGTCACCGAGCAGGACAGCAAGGACTCCACCTACAGCCTG
AGCAGCACCCTGACCCTGAGCAAGGCCGACTACGAGAAGCACAAGGTGTA
CGCCTGTGAGGTGACCCACCAGGGCCTGTCCAGCCCCGTGACCAAGAGCT
TCAACAGGGGCGAGTGCTGATGA BAN0805 VH gene with signal sequence
(SEQ ID NO: 13)
ATGGAATGGTCCTGGGTGTTCCTGTTCTTCCTGTCCGTGACCACCGGCGT
GCACTCTCAGGTTCAGCTGCAAGAGTCTGGCCCTGGCCTGGTCAAGCCTT
CCGAAACACTGTCTCTGACCTGCACCGTGTCCGGCTTCTCCCTGACATCT
TATGGGGTGCACTGGATCAGACAGCCTCCAGGCAAAGGCCTGGAATGGAT
CGGAGTGATTTGGAGAGGCGGCTCCACCGATTACTCCGCCGCCTTCATGT
CCCGGCTGACCATCTCTAAGGACACCTCCAAGAACCAGGTGTCCCTGAAG
CTGTCCTCTGTGACCGCTGCTGATACCGCCGTGTACTACTGTGCCAAGCT
GCTGAGATCTGTCGGCGGCTTTGCTGATTGGGGCCAGGGCACAATGGTCA
CCGTGTCTAGCGC BAN0805 VL gene with signal sequence
(SEQ ID NO: 14)
ATGTCTGTGCCTACACAGGTTCTGGGACTGCTGCTGCTGTGGCTGACCGA
CGCCAGATGCGACATCGTGATGACCCAGTCTCCACTGAGCCTGCCTGTGA
CACCTGGCGAGCCTGCTTCCATCTCCTGCAGATCCTCTCAGACCATCGTG
CACAACAACGGCAACACCTACCTGGAATGGTATCTGCAGAAGCCCGGCCA
GTCTCCTCAGCTGCTGATCTACAAGGTGTCCAACCGGTTCTCTGGCGTGC
CCGACAGATTTTCCGGCTCTGGCTCTGGCACCGACTTCACCCTGAAGATC
TCCAGAGTGGAAGCCGAGGACGTGGGCGTGTACTACTGCTTCCAAGGCTC
TCACGTGCCCTTCACCTTTGGCCAGGGCACCAAGCTGGAAATCAAG BAN0805 HC gene
(SEQ ID NO: 17)
CAGGTTCAGCTGCAAGAGTCTGGCCCTGGCCTGGTCAAGCCTTCCGAAAC
ACTGTCTCTGACCTGCACCGTGTCCGGCTTCTCCCTGACATCTTATGGGG
TGCACTGGATCAGACAGCCTCCAGGCAAAGGCCTGGAATGGATCGGAGTG
ATTTGGAGAGGCGGCTCCACCGATTACTCCGCCGCCTTCATGTCCCGGCT
GACCATCTCTAAGGACACCTCCAAGAACCAGGTGTCCCTGAAGCTGTCCT
CTGTGACCGCTGCTGATACCGCCGTGTACTACTGTGCCAAGCTGCTGAGA
TCTGTCGGCGGCTTTGCTGATTGGGGCCAGGGCACAATGGTCACCGTGTC
TAGCGCTTCTACAAAGGGCCCAAGCGTGTTCCCCCTGGCCCCCTGCTCCA
GAAGCACCAGCGAGAGCACAGCCGCCCTGGGCTGCCTGGTGAAGGACTAC
TTCCCCGAGCCCGTGACCGTGTCCTGGAACAGCGGAGCCCTGACCAGCGG
CGTGCACACCTTCCCCGCCGTGCTGCAGAGCAGCGGCCTGTACAGCCTGA
GCAGCGTGGTGACCGTGCCCAGCAGCAGCCTGGGCACCAAGACCTACACC
TGTAACGTGGACCACAAGCCCAGCAACACCAAGGTGGACAAGAGGGTGGA
GAGCAAGTACGGCCCACCCTGCCCCCCCTGCCCAGCCCCGAGTTCCTGG
GCGGACCCAGCGTGTTCCTGTTCCCCCCAAGCCCAAGGACACCCTGATG
ATCAGCAGAACCCCCGAGGTGACCTGTGTGGTGGTGGACGTGTCCCAGGA
GGACCCCGAGGTCCAGTTCAACTGGTACGTGGACGGCGTGGAGGTGCACA
ACGCCAAGACCAAGCCCAGAGAGGAGCAGTTTAACAGCACCTACCGGGTG
GTGTCCGTGCTGACCGTGCTGCACCAGGACTGGCTGAACGGCAAAGAGTA
CAAGTGTAAGGTCTCCAACAAGGGCCTGCCAAGCAGCATCGAAAAGACCA
TCAGCAAGGCCAAGGGCCAGCCTAGAGAGCCCCAGGTCTACACCCTGCCA
CCCAGCCAAGAGGAGATGACCAAGAACCAGGTGTCCCTGACCTGTCTGGT
GAAGGGCTTCTACCCAAGCGACATCGCCGTGGAGTGGGAGAGCAACGGCC
AGCCCGAGAACAACTACAAGACCACCCCCCAGTGCTGGACAGCGACGGC
AGCTTCTTCCTGTACAGCAGGCTGACCGTGGACAAGTCCAGATGGCAGGA
GGGCAACGTCTTTAGCTGCTCCGTGATGCACGAGGCCCTGCACAACCACT
ACACCCAGAAGAGCCTGAGCCTGTCCCTGGGCTGA BAN0805 LC gene
(SEQ ID NO: 18)
GACATCGTGATGACCCAGTCTCCACTGAGCCTGCCTGTGACACCTGGCGA
GCCTGCTTCCATCTCCTGCAGATCCTCTCAGACCATCGTGCACAACAACG
GCAACACCTACCTGGAATGGTATCTGCAGAAGCCCGGCCAGTCTCCTCAG
CTGCTGATCTACAAGGTGTCCAACCGGTTCTCTGGCGTGCCCGACAGATT
TTCCGGCTCTGGCTCTGGCACCGACTTCACCCTGAAGATCTCCAGAGTGG
AAGCCGAGGACGTGGGCGTGTACTACTGCTTCCAAGGCTCTCACGTGCCC
TTCACCTTTGGCCAGGGCACCAAGCTGGAAATCAAGCGTACGGTGGCCGC
TCCCAGCGTGTTCATCTTCCCCCCAAGCGACGAGCAGCTGAAGAGCGGCA
CCGCCAGCGTGGTGTGTCTGCTGAACAACTTCTACCCCAGGGAGGCCAAG
GTGCAGTGGAAGGTGGACAACGCCCTGCAGAGCGGCAACAGCCAGGAGAG
CGTCACCGAGCAGGACAGCAAGGACTCCACCTACAGCCTGAGCAGCACCC
TGACCCTGAGCAAGGCCGACTACGAGAAGCACAAGGTGTACGCCTGTGAG
GTGACCCACCAGGGCCTGTCCAGCCCCGTGACCAAGAGCTTCAACAGGGG
CGAGTGCTGA BAN0805 VH gene
(SEQ ID NO: 19)
CAGGTTCAGCTGCAAGAGTCTGGCCCTGGCCTGGTCAAGCCTTCCGAAAC
ACTGTCTCTGACCTGCACCGTGTCCGGCTTCTCCCTGACATCTTATGGGG
TGCACTGGATCAGACAGCCTCCAGGCAAAGGCCTGGAATGGATCGGAGTG
ATTTGGAGAGGCGGCTCCACCGATTACTCCGCCGCCTTCATGTCCCGGCT
GACCATCTCTAAGGACACCTCCAAGAACCAGGTGTCCCTGAAGCTGTCCT
CTGTGACCGCTGCTGATACCGCCGTGTACTACTGTGCCAAGCTGCTGAGA
TCTGTCGGCGGCTTTGCTGATTGGGGCCAGGGCACAATGGTCACCGTGTC
TAGCGC BAN0805 VL gene
(SEQ ID NO: 20)
GACATCGTGATGACCCAGTCTCCACTGAGCCTGCCTGTGACACCTGGCGA
GCCTGCTTCCATCTCCTGCAGATCCTCTCAGACCATCGTGCACAACAACG
GCAACACCTACCTGGAATGGTATCTGCAGAAGCCCGGCCAGTCTCCTCAG
CTGCTGATCTACAAGGTGTCCAACCGGTTCTCTGGCGTGCCCGACAGATT
TTCCGGCTCTGGCTCTGGCACCGACTTCACCCTGAAGATCTCCAGAGTGG
AAGCCGAGGACGTGGGCGTGTACTACTGCTTCCAAGGCTCTCACGTGCCC
TTCACCTTTGGCCAGGGCACCAAGCTGGAAATCAAG The sequences encoding a signal peptide are underlined. The start codons are in bold and the stop codons are in italic.

What is claimed is:

1. An antibody comprising a heavy chain comprising the amino acid sequence of SEQ ID NO: 1 and a light chain comprising the amino acid sequence of SEQ ID NO: 2.

2. The antibody of claim 1, wherein the antibody is of the IgG isotype.

3. The antibody of claim 2, wherein the antibody is of the IgG4 isotype.

4. The antibody of claim 1, wherein the antibody has a $K_D$ value for binding the protofibril form of α-synuclein at least 110,000 times smaller than the $K_D$ value for binding the monomeric form of α-synuclein.

5. The antibody of claim 4, wherein the $K_D$ of said antibody for binding to the protofibril form of α-synuclein and the $K_D$ of said antibody for binding to the monomeric form of α-synuclein are measured by SPR.

6. The antibody of claim 1, wherein the antibody has a $K_D$ value for binding the protofibril form of α-synuclein of at most 18 pM and a $K_D$ value for binding the monomeric form of α-synuclein of at least 2200 nM.

7. The antibody of claim 6, wherein the $K_D$ of said antibody for binding to the protofibril form of α-synuclein and the $K_D$ of said antibody for binding to the monomeric form of α-synuclein are measured by SPR.

8. One or more nucleic acids encoding the antibody of claim 1.

9. The one or more nucleic acids of claim 8, wherein
(a) the one or more nucleic acids comprise the sequences of SEQ ID NOs: 11 and 12,
(b) the one or more nucleic acids comprise the sequences of SEQ ID NOs: 13 and 14,
(c) the one or more nucleic acids comprise the sequences of SEQ ID NOs: 17 and 18, or
(d) the one or more nucleic acids comprise the sequences of SEQ ID NOs: 19 and 20.

10. A host cell expressing the antibody of claim 1.

11. A composition comprising the antibody of claim 1 and a pharmaceutically acceptable carrier.

12. An antibody comprising a heavy chain comprising the amino acid sequence of SEQ ID NO:3 and a light chain comprising the amino acid sequence of SEQ ID NO:4.

13. The antibody of claim 12, wherein the antibody comprises two heavy chains and two light chains.

14. One or more nucleic acids encoding the antibody of claim 12.

15. The one or more nucleic acids of claim 14, wherein
(a) the one or more nucleic acids comprise the sequences of SEQ ID NOs: 11 and 12,
(b) the one or more nucleic acids comprise the sequences of SEQ ID NOs: 13 and 14,
(c) the one or more nucleic acids comprise the sequences of SEQ ID NOs: 17 and 18, or
(d) the one or more nucleic acids comprise the sequences of SEQ ID NOs: 19 and 20.

16. A host cell expressing the antibody of claim 12.

17. A composition comprising the antibody of claim 12 and a pharmaceutically acceptable carrier.

18. A nucleic acid encoding a polypeptide comprising an amino acid sequence selected from the group consisting of SEQ ID NOs: 1-4.

19. A host cell comprising the nucleic acid(s) of claim 18.

20. One or more vectors comprising the nucleic acid(s) of claim 18.

21. A host cell comprising the one or more vector(s) of claim 20.

22. The nucleic acid of claim 18, comprising a sequence selected from the group consisting of SEQ ID NOs: 11-14 and 17-20.

23. A host cell comprising the nucleic acid(s) of claim 22.

24. One or more vectors comprising the nucleic acid(s) of claim 22.

25. A host cell comprising the one or more vector(s) of claim 24.

* * * * *

SEQUENCE LISTING

<160> NUMBER OF SEQ ID NOS: 20

<210> SEQ ID NO 1
<211> LENGTH: 118
<212> TYPE: PRT
<213> ORGANISM: artificial
<220> FEATURE:
<223> OTHER INFORMATION: BAN0805 VH

<400> SEQUENCE: 1

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val His Trp Ile Arg Gln Pro Pro Gly Lys Gly Leu Glu Trp Ile
        35                  40                  45

Gly Val Ile Trp Arg Gly Gly Ser Thr Asp Tyr Ser Ala Ala Phe Met
    50                  55                  60

Ser Arg Leu Thr Ile Ser Lys Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys Leu Leu Arg Ser Val Gly Gly Phe Ala Asp Trp Gly Gln Gly Thr
            100                 105                 110

Met Val Thr Val Ser Ser
        115
```

<210> SEQ ID NO 2
<211> LENGTH: 112
<212> TYPE: PRT
<213> ORGANISM: artificial
<220> FEATURE:
<223> OTHER INFORMATION: BAN0805 VL

<400> SEQUENCE: 2

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Thr Ile Val His Asn
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Phe Thr Phe Gly Gln Gly Thr Lys Leu Glu Ile Lys
            100                 105                 110
```

<210> SEQ ID NO 3
<211> LENGTH: 444
<212> TYPE: PRT
<213> ORGANISM: artificial
<220> FEATURE:
<223> OTHER INFORMATION: BAN0805 Heavy Chain

<400> SEQUENCE: 3

```
Gln Val Gln Leu Gln Glu Ser Gly Pro Gly Leu Val Lys Pro Ser Glu
1               5                   10                  15
```

```
Thr Leu Ser Leu Thr Cys Thr Val Ser Gly Phe Ser Leu Thr Ser Tyr
            20                  25                  30

Gly Val His Trp Ile Arg Gln Pro Gly Lys Gly Leu Glu Trp Ile
            35                  40                  45

Gly Val Ile Trp Arg Gly Gly Ser Thr Asp Tyr Ser Ala Ala Phe Met
50                  55                  60

Ser Arg Leu Thr Ile Ser Lys Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Lys Leu Leu Arg Ser Val Gly Gly Phe Ala Asp Trp Gly Gln Gly Thr
            100                 105                 110

Met Val Thr Val Ser Ser Ala Ser Thr Lys Gly Pro Ser Val Phe Pro
            115                 120                 125

Leu Ala Pro Cys Ser Arg Ser Thr Ser Glu Ser Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
            195                 200                 205

Asn Thr Lys Val Asp Lys Arg Val Glu Ser Lys Tyr Gly Pro Pro Cys
210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
275                 280                 285

Pro Arg Glu Glu Gln Phe Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430
```

His Tyr Thr Gln Lys Ser Leu Ser Leu Ser Leu Gly
        435                 440

<210> SEQ ID NO 4
<211> LENGTH: 219
<212> TYPE: PRT
<213> ORGANISM: artificial
<220> FEATURE:
<223> OTHER INFORMATION: BAN0805 Light Chain

<400> SEQUENCE: 4

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Thr Ile Val His Asn
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Phe Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 5
<211> LENGTH: 10
<212> TYPE: PRT
<213> ORGANISM: artificial
<220> FEATURE:
<223> OTHER INFORMATION: BAN0805 VH-CDR-1 (Chothia)

<400> SEQUENCE: 5

Gly Phe Ser Leu Thr Ser Tyr Gly Val His
1               5                   10

<210> SEQ ID NO 6
<211> LENGTH: 14
<212> TYPE: PRT
<213> ORGANISM: artificial
<220> FEATURE:
<223> OTHER INFORMATION: BAN0805 VH-CDR-2 (Chothia)

<400> SEQUENCE: 6

Val Ile Trp Arg Gly Gly Ser Thr Asp Tyr Ser Ala Ala Phe

<210> SEQ ID NO 7
<211> LENGTH: 10
<212> TYPE: PRT
<213> ORGANISM: artificial
<220> FEATURE:
<223> OTHER INFORMATION: BAN0805 VH-CDR-3 (Kabat/Chothia)

<400> SEQUENCE: 7

Leu Leu Arg Ser Val Gly Gly Phe Ala Asp
1               5                   10

<210> SEQ ID NO 8
<211> LENGTH: 16
<212> TYPE: PRT
<213> ORGANISM: artificial
<220> FEATURE:
<223> OTHER INFORMATION: BAN0805 VL-CDR-1 (Kabat/Chothia)

<400> SEQUENCE: 8

Arg Ser Ser Gln Thr Ile Val His Asn Asn Gly Asn Thr Tyr Leu Glu
1               5                   10                  15

<210> SEQ ID NO 9
<211> LENGTH: 7
<212> TYPE: PRT
<213> ORGANISM: artificial
<220> FEATURE:
<223> OTHER INFORMATION: BAN0805 VL-CDR-2 (Kabat/Chothia)

<400> SEQUENCE: 9

Lys Val Ser Asn Arg Phe Ser
1               5

<210> SEQ ID NO 10
<211> LENGTH: 9
<212> TYPE: PRT
<213> ORGANISM: artificial
<220> FEATURE:
<223> OTHER INFORMATION: BAN0805 VL-CDR-3 (Kabat/Chothia)

<400> SEQUENCE: 10

Phe Gln Gly Ser His Val Pro Phe Thr
1               5

<210> SEQ ID NO 11
<211> LENGTH: 1395
<212> TYPE: DNA
<213> ORGANISM: artificial
<220> FEATURE:
<223> OTHER INFORMATION: BAN0805 HC gene with signal sequence

<400> SEQUENCE: 11
atggaatggt cctgggtgtt cctgttcttc ctgtccgtga ccaccggcgt gcactctcag      60
gttcagctgc aagagtctgg ccctggcctg gtcaagcctt ccgaaacact gtctctgacc     120
tgcaccgtgt ccggcttctc cctgacatct tatgggtgc actggatcag acagcctcca     180
ggcaaaggcc tggaatggat cggagtgatt tggagaggcg gctccaccga ttactccgcc     240
gccttcatgt cccggctgac catctctaag gacacctcca gaaccaggt gtccctgaag     300 ctgtcctctg tgaccgctgc tgataccgcc gtgtactact gtgccaagct gctgagatct     360
gtcggcggct tgctgattg gggccagggc acaatggtca ccgtgtctag cgcttctaca     420
aagggcccaa gcgtgttccc cctggccccc tgctccagaa gcaccagcga gagcacagcc     480

```
gccctgggct gcctggtgaa ggactacttc cccgagcccg tgaccgtgtc ctggaacagc      540
ggagccctga ccagcggcgt gcacaccttc ccgccgtgc tgcagagcag cggcctgtac       600
agcctgagca gcgtggtgac cgtgcccagc agcagcctgg gcaccaagac ctacacctgt      660
aacgtggacc acaagcccag caacaccaag gtggacaaga gggtggagag caagtacggc      720 ccacccctgcc ccccctgccc agccccgag ttcctgggcg acccagcgt gttcctgttc       780 cccccaagc caaggacac cctgatgatc agcagaaccc cgaggtgac ctgtgtggtg         840 gtggacgtgt cccaggagga ccccgaggtc cagttcaact ggtacgtgga cggcgtggag      900
gtgcacaacg ccaagaccaa gcccagagag gagcagttta cagcaccta ccgggtggtg      960 tccgtgctga ccgtgctgca ccaggactgg ctgaacggca agagtacaa gtgtaaggtc      1020 tccaacaagg gcctgccaag cagcatcgaa aagaccatca gcaaggccaa gggccagcct      1080
agagagcccc aggtctacac cctgccaccc agccaagagg agatgaccaa gaaccaggtg      1140
tccctgacct gtctggtgaa gggcttctac ccaagcgaca tcgccgtgga gtgggagagc      1200
aacggccagc ccgagaacaa ctacaagacc accccccag tgctggacag cgacggcagc      1260
ttcttcctgt acagcaggct gaccgtggac aagtccagat ggcaggaggg caacgtcttt      1320
agctgctccg tgatgcacga ggccctgcac aaccactaca cccagaagag cctgagcctg      1380
tccctgggct gatga                                                      1395

<210> SEQ ID NO 12
<211> LENGTH: 723
<212> TYPE: DNA
<213> ORGANISM: artificial
<220> FEATURE:
<223> OTHER INFORMATION: BAN0805 LC gene with signal sequence

<400> SEQUENCE: 12
atgtctgtgc ctacacaggt tctgggactg ctgctgctgt ggctgaccga cgccagatgc       60
gacatcgtga tgacccagtc tccactgagc ctgcctgtga cacctggcga gcctgcttcc      120
atctcctgca gatcctctca gaccatcgtg cacaacaacg gcaacaccta cctggaatgg      180
tatctgcaga agccccggcca gtctcctcag ctgctgatct acaaggtgtc caaccggttc      240
tctggcgtgc ccgacagatt ttccggctct ggctctggca ccgacttcac cctgaagatc      300
tccagagtgg aagccgagga cgtgggcgtg tactactgct ccaaggctc tcacgtgccc      360 ttcacctttg gccagggcac caagctggaa atcaagcgta cggtggccgc tcccagcgtg      420
ttcatcttcc ccccaagcga cgagcagctg aagagcggca ccgccagcgt ggtgtgtctg      480
ctgaacaact tctaccccag ggaggccaag gtgcagtgga aggtggacaa cgccctgcag      540
agcggcaaca gccaggagag cgtcaccgag caggacagca aggactccac ctacagcctg      600
agcagcaccc tgaccctgag caaggccgac tacgagaagc acaaggtgta cgcctgtgag      660
gtgacccacc agggcctgtc cagcccgtg accaagagct caacaggggg cgagtgctga      720
tga                                                                    723

<210> SEQ ID NO 13
<211> LENGTH: 413
<212> TYPE: DNA
<213> ORGANISM: artificial
<220> FEATURE:
<223> OTHER INFORMATION: BAN0805 VH gene with signal sequence

<400> SEQUENCE: 13
```

```
atggaatggt cctgggtgtt cctgttcttc ctgtccgtga ccaccggcgt gcactctcag    60
gttcagctgc aagagtctgg ccctggcctg gtcaagcctt ccgaaacact gtctctgacc   120
tgcaccgtgt ccggcttctc cctgacatct tatggggtgc actggatcag acagcctcca   180
ggcaaaggcc tggaatggat cggagtgatt tggagaggcg gctccaccga ttactccgcc   240
gccttcatgt cccggctgac catctctaag gacacctcca agaaccaggt gtccctgaag   300
ctgtcctctg tgaccgctgc tgataccgcc gtgtactact gtgccaagct gctgagatct   360
gtcggcggct ttgctgattg gggccagggc acaatggtca ccgtgtctag cgc          413

<210> SEQ ID NO 14
<211> LENGTH: 396
<212> TYPE: DNA
<213> ORGANISM: artificial
<220> FEATURE:
<223> OTHER INFORMATION: BAN0805 VL gene with signal sequence

<400> SEQUENCE: 14
atgtctgtgc ctacacaggt tctgggactg ctgctgctgt ggctgaccga cgccagatgc    60
gacatcgtga tgacccagtc tccactgagc ctgcctgtga cacctggcga gcctgcttcc   120
atctcctgca gatcctctca gaccatcgtg cacaacaacg gcaacaccta cctggaatgg   180
tatctgcaga agcccggcca gtctcctcag ctgctgatct acaaggtgtc caaccggttc   240
tctggcgtgc ccgacagatt tccggctct ggctctggca ccgacttcac cctgaagatc   300
tccagagtgg aagccgagga cgtgggcgtg tactactgct ccaaggctc tcacgtgccc   360 ttcacctttg gcagggcac caagctggaa atcaag                              396

<210> SEQ ID NO 15
<211> LENGTH: 5
<212> TYPE: PRT
<213> ORGANISM: artificial
<220> FEATURE:
<223> OTHER INFORMATION: BAN0805 VH-CDR-1 (Kabat)

<400> SEQUENCE: 15

Ser Tyr Gly Val His
1               5

<210> SEQ ID NO 16
<211> LENGTH: 16
<212> TYPE: PRT
<213> ORGANISM: artificial
<220> FEATURE:
<223> OTHER INFORMATION: BAN0805 VH-CDR-2 (Kabat)

<400> SEQUENCE: 16

Val Ile Trp Arg Gly Gly Ser Thr Asp Tyr Ser Ala Ala Phe Met Ser
1               5                   10                  15

<210> SEQ ID NO 17
<211> LENGTH: 1335
<212> TYPE: DNA
<213> ORGANISM: artificial
<220> FEATURE:
<223> OTHER INFORMATION: BAN0805 HC gene

<400> SEQUENCE: 17
caggttcagc tgcaagagtc tggccctggc ctggtcaagc cttccgaaac actgtctctg    60
acctgcaccg tgtccggctt ctcccctgaca tcttatgggg tgcactggat cagacagcct   120
ccaggcaaag gcctggaatg gatcggagtg atttggagag gcggctccac cgattactcc   180
```

```
gccgccttca tgtcccggct gaccatctct aaggacacct ccaagaacca ggtgtccctg      240
aagctgtcct ctgtgaccgc tgctgatacc gccgtgtact actgtgccaa gctgctgaga      300
tctgtcggcg ctttgctga ttggggccag ggcacaatgg tcaccgtgtc tagcgcttct       360
acaaagggcc caagcgtgtt ccccctggcc cctgctcca gaagcaccag cgagagcaca       420
gccgccctgg gctgcctggt gaaggactac ttccccgagc ccgtgaccgt gtcctggaac      480
agcggagccc tgaccagcgg cgtgcacacc ttccccgccg tgctgcagag cagcggcctg      540
tacagcctga gcagcgtggt gaccgtgccc agcagcagcc tgggcaccaa gacctacacc      600
tgtaacgtgg accacaagcc cagcaacacc aaggtggaca gagggtggag agcaagtac       660 ggcccaccct gccccccctg cccagccccc gagttcctgg gcggaccag cgtgttcctg       720 ttccccccca gcccaagga caccctgatg atcagcagaa cccccgaggt gacctgtgtg       780
gtggtggacg tgtcccagga ggaccccgag gtccagttca actggtacgt ggacggcgtg      840
gaggtgcaca cgccaagac caagcccaga gaggagcagt taacagcac ctaccgggtg       900 gtgtccgtgc tgaccgtgct gcaccaggac tggctgaacg gcaaagagta caagtgtaag      960
gtctccaaca agggcctgcc aagcagcatc gaaaagacca tcagcaaggc caagggccag     1020
cctagagagc cccaggtcta caccctgcca cccagccaag aggagatgac caagaaccag     1080
gtgtccctga cctgtctggt gaagggcttc tacccaagcg acatcgccgt ggagtgggag     1140
agcaacggcc agcccgagaa caactacaag accacccccc cagtgctgga cagcgacggc     1200
agcttcttcc tgtacagcag gctgaccgtg gacaagtcca gatggcagga gggcaacgtc     1260
tttagctgct ccgtgatgca cgaggccctg cacaaccact acacccagaa gagcctgagc     1320
ctgtccctgg gctga                                                      1335

<210> SEQ ID NO 18
<211> LENGTH: 660
<212> TYPE: DNA
<213> ORGANISM: artificial
<220> FEATURE:
<223> OTHER INFORMATION: BAN0805 LC gene

<400> SEQUENCE: 18
gacatcgtga tgacccagtc tccactgagc ctgcctgtga cacctggcga gcctgcttcc       60
atctcctgca gatcctctca gaccatcgtg cacaacaacg gcaacaccta cctggaatgg      120
tatctgcaga agcccggcca gtctcctcag ctgctgatct acaaggtgtc caaccggttc      180
tctggcgtgc ccgacagatt ttccggctct ggctctggca ccgacttcac cctgaagatc      240
tccagagtgg aagccgagga cgtgggcgtg tactactgct cccaaggctc tcacgtgccc      300
ttcacctttg gccagggcac caagctggaa atcaagcgta cggtggccgc tcccagcgtg      360
ttcatcttcc ccccaagcga cgagcagctg aagagcggca ccgccagcgt ggtgtgtctg      420
ctgaacaact tctaccccag ggaggccaag gtgcagtgga aggtggacaa cgccctgcag      480
agcggcaaca gccaggagag cgtcaccgag caggacagca aggactccac ctacagcctg      540
agcagcaccc tgaccctgag caaggccgac tacgagaagc acaaggtgta cgcctgtgag      600
gtgacccacc agggcctgtc cagccccgtg accaagagct caacagggg cgagtgctga      660

<210> SEQ ID NO 19
<211> LENGTH: 356
<212> TYPE: DNA
<213> ORGANISM: artificial
<220> FEATURE:
```

-continued

```
<223> OTHER INFORMATION: BAN0805 VH gene

<400> SEQUENCE: 19
caggttcagc tgcaagagtc tggccctggc ctggtcaagc cttccgaaac actgtctctg      60
acctgcaccg tgtccggctt ctccctgaca tcttatgggg tgcactggat cagacagcct    120
ccaggcaaag gcctggaatg gatcggagtg atttggagag gcggctccac cgattactcc    180
gccgccttca tgtcccggct gaccatctct aaggacacct ccaagaacca ggtgtccctg    240
aagctgtcct ctgtgaccgc tgctgatacc gccgtgtact actgtgccaa gctgctgaga    300
tctgtcggcg gctttgctga ttggggccag ggcacaatgg tcaccgtgtc tagcgc        356

<210> SEQ ID NO 20
<211> LENGTH: 336
<212> TYPE: DNA
<213> ORGANISM: artificial
<220> FEATURE:
<223> OTHER INFORMATION: BAN0805 VL gene

<400> SEQUENCE: 20
gacatcgtga tgacccagtc tccactgagc ctgcctgtga cacctggcga gcctgcttcc     60
atctcctgca gatcctctca gaccatcgtg cacaacaacg gcaacaccta cctggaatgg    120
tatctgcaga gcccggcca gtctcctcag ctgctgatct acaaggtgtc caaccggttc    180
tctggcgtgc ccgacagatt ttccggctct ggctctggca ccgacttcac cctgaagatc    240
tccagagtgg aagccgagga cgtgggcgtg tactactgct tccaaggctc tcacgtgccc    300
ttcacctttg gccagggcac caagctggaa atcaag                              336
```